(12) United States Patent
Wu et al.

(10) Patent No.: US 11,345,942 B2
(45) Date of Patent: May 31, 2022

(54) SOLID MEDIUM FOR PRODUCING GLUCOSAMINE AND ITS APPLICATION

(71) Applicant: YUAN ZE UNIVERSITY, Taoyuan (TW)

(72) Inventors: Ho-Shing Wu, Taoyuan (TW); Jia-Wei Peng, Taoyuan (TW)

(73) Assignee: YUAN ZE UNIVERSITY, Taoyuan (TW)

( * ) Notice: Subject to any disclaimer, the term of this patent is extended or adjusted under 35 U.S.C. 154(b) by 247 days.

(21) Appl. No.: 16/562,529

(22) Filed: Sep. 6, 2019

(65) Prior Publication Data

US 2020/0087693 A1    Mar. 19, 2020

(30) Foreign Application Priority Data

Sep. 17, 2018    (TW) ................. 107132647

(51) Int. Cl.
| | |
|---|---|
| C12P 19/26 | (2006.01) |
| C12N 1/16 | (2006.01) |
| C12N 5/00 | (2006.01) |
| C12N 1/00 | (2006.01) |
| C12N 1/14 | (2006.01) |

(52) U.S. Cl.
CPC ............. *C12P 19/26* (2013.01); *C12N 1/00* (2013.01); *C12N 1/14* (2013.01); *C12N 1/16* (2013.01); *C12N 5/0018* (2013.01); *C12N 2500/16* (2013.01); *C12N 2500/30* (2013.01)

(58) Field of Classification Search
CPC . C12P 19/26; C12P 19/02; C12N 1/14; C12N 1/16; C12N 5/0018; C12N 1/00; C12N 2500/30; C12N 2500/16
See application file for complete search history.

(56) References Cited

U.S. PATENT DOCUMENTS

| | | | | |
|---|---|---|---|---|
| 1,687,561 A * | 10/1928 | Hoffman | ......... | C12N 1/18 127/50 |
| 1,769,469 A * | 7/1930 | Shafor | ......... | C13B 35/04 127/47 |
| 7,332,304 B2 * | 2/2008 | Deng | ......... | C12P 19/26 435/84 |
| 2011/0269185 A1 * | 11/2011 | David | ......... | C12N 1/18 435/69.1 |

FOREIGN PATENT DOCUMENTS

CN    102273487 A    * 12/2011

OTHER PUBLICATIONS

Omidvar et al. Enhanced ethanol and glucosamine production from rice husk by NAOH pretreatment and fermentation by fungus Mucor hiemalis. Biofuel Research Journal (2016), 475-481. (Year: 2016).*
Roopesh et al. Comparison of phytase production on wheat bran and oilcakes in solid-state fermentation by Mucor racemosus. Bioresource Technology (2006), 97(3), 506-511. (Year: 2006).*
Ibrahim et al. Characterization of Solid State Fermentation Culture Conditions for Growth and Mananase Production by Aspergillus niger USM F4 on Rice Husk in Tray System. British Technology Journal (2012), 2(3), 133-145. (Year: 2012).*
Alegre et al. Ethanol Fermentation of a Diluted Molasses Medium by *Saccharomyces cerevisiae* Immobilized on Chrysotile. Brazillian Archives of Biology and Technology (2003), 46(4), 751-757. (Year: 2003).*
Pisarevskaya et al. Changes in the Composition of Cell Walls in the Process of Absidia-Coerulea Cyto Differentiation Related to the Formation of Resting Structures. Mikrobiologiya (1983), 52 (1), 124-130. (Year: 1983).*
Wu et al. Effect of Oxygen Transfer and Pellet Size for Producing of Glucosamine Using Aspergillus sydowii BCRC 31742 Cultivated in a Fermenter. J. Food Process Technol (2017), 8(10), 1000697, 5 pages. (Year: 2017).*
Hsieh et al. Determination and Kinetics of Producing Glucosamine Using Fungi. Biotechnol. Prog. (2007), 23, 1009-1016. (Year: 2007).*
Chang et al. Journal of Food Technology (2011), 9(2): 75-82. Optimizing Biotechnological Production of Glucosamine as Food Ingredient from *Aspergillus* sp. BCRC 31742. (Year: 2011).*
Kanauchi et al. Role of extract from cocklebur leaves used for wheat-qu (koji) making described in Chinese old literature Chimin yao shu. J. Brew. Soc. Japan. (1998), 93(11), 910-915, and appended translation. (Year: 1998).*

* cited by examiner

*Primary Examiner* — Sean C. Barron

(74) *Attorney, Agent, or Firm* — Locke Lord LLP; Tim Tingkang Xia, Esq.

(57) ABSTRACT

The invention relates to solid medium for producing glucosamine, including a substrate and 0.15-4.8 mL/g substrate of supplemental solution, which includes 0.1-2 g/L $KH_2PO_4$, 0.1-2 g/L NaCl, and 0.1-2 g/L $MgSO_4.7H_2O$. The invention also relates to a method for producing glucosamine, including providing microorganism being able to produce glucosamine, and fermenting the microorganism in the medium mentioned above.

8 Claims, 8 Drawing Sheets

SOLID MEDIUM FOR PRODUCING GLUCOSAMINE AND ITS APPLICATION

CROSS-REFERENCE TO RELATED APPLICATION

This application claims priority to Taiwan Application Serial Number 107132647, filed on Sep. 17, 2018, which is herein incorporated by reference.

BACKGROUND OF THE INVENTION

1. Field of the Invention

The present invention relates to a solid medium for producing glucosamine, particularly to solid medium using coffee grounds, and/or rice bran, and/or wheat bran as substrate to reduce production costs and increase yields of glucosamine, and application of the medium.

2. Description of the Prior Art

Glucosamine is one of the key components of cartilage and has been extensively used to treat osteoarthritis and rheumatoid arthritis. It has also been proven that glucosamine inhibits the proliferation and induces apoptosis of leukemia cells. In addition, glucosamine possesses natural anti-inflammatory and anti-aging properties. Glucosamine is deemed to be a natural and harmless compound and therefore is widely used as food supplements in some countries in Europe and America.

There are three major ways to produce glucosamine: acid hydrolysis, enzymatic hydrolysis, and microbial fermentation. Traditionally, glucosamine is derived from hydrolysis of chitin and/or chitosan by strong acids (such as hydrochloric acid and nitric acid), which causes problems of acid waste treatment.

Enzymatic hydrolysis of chitin and chitosan to produce glucosamine causes fewer problems about waste treatment. There are many options of enzymes for producing glucosamine, and the most commonly used ones include chitinase and chitosanase. However, in addition to the high prices of the enzymes, enzymatic hydrolysis efficiency is quite low due to the poor water-solubility of chitin and chitosan. Therefore, enzymatic production of glucosamine still cannot be commercialized due to high production costs and low yields.

At present, industrial production of glucosamine is mainly carried out by acid hydrolysis of shrimp and crab shells. However, the sources of the shells may affect the purity of glucosamine, and glucosamine produced from contaminated shells may be toxic. Furthermore, washing shrimp and crab shells to prevent stink before hydrolysis and additional purification processes to remove other by-products that may cause allergies in humans are both time consuming and increase production costs. Based on all the disadvantages described above, production of glucosamine by microorganisms may be a better option than traditional acid hydrolysis.

In addition to acid and enzymatic hydrolysis, specific microorganisms can produce glucosamine as well. Compared to hydrolysis, production of glucosamine by microorganisms is not limited by reactors or the source of raw materials, has short production cycle time, provides glucosamine consistently, and causes very few environmental problems. In addition, glucosamine produced by microbial fermentation is free from stinks and heavy metal contamination and does not cause allergies in humans. Therefore, production of glucosamine by microorganisms is drawing more and more attention of researchers. However, low yields and high production costs of glucosamine produced by microbial fermentation are still some problems that need to be solved.

Industrial production of glucosamine by microorganisms is carried out by liquid fermentation. However, liquid fermentation requires a huge amount of liquid, which is usually more than 20 times the volume of the medium required for solid fermentation. Therefore, liquid fermentation needs a large fermentation tank, resulting in intense management and high costs. In addition, it take up to 5 days to produce glucosamine by liquid fermentation, and the operation of the fermentation tank requires a large amount of energy, which also results in high costs. Therefore, it is important to develop new media for producing glucosamine to increase yields and reduce production costs of glucosamine.

SUMMARY OF THE INVENTION

The first aspect of the present invention relates to a solid medium for producing glucosamine, comprising substrate and 0.15-4.8 mL/g substrate of supplemental solution, which includes 0.1-2 g/L $KH_2PO_4$, 0.1-2 g/L NaCl, and 0.1-2 g/L $MgSO_4.7H_2O$.

The second aspect of the present invention relates to a method for producing glucosamine, comprising:
providing a microorganism being able to produce glucosamine; and
fermenting the microorganism in a solid medium;
wherein the solid medium comprises substrate and 0.15-4.8 mL/g substrate of supplemental solution, which includes 0.1-2 g/L $KH_2PO_4$, 0.1-2 g/L NaCl, and 0.1-2 g/L $MgSO_4.7H_2O$.

These and other aspects of the present invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment, and wherein.

DETAILED DESCRIPTION OF THE PREFERRED EMBODIMENT

Figure 1:
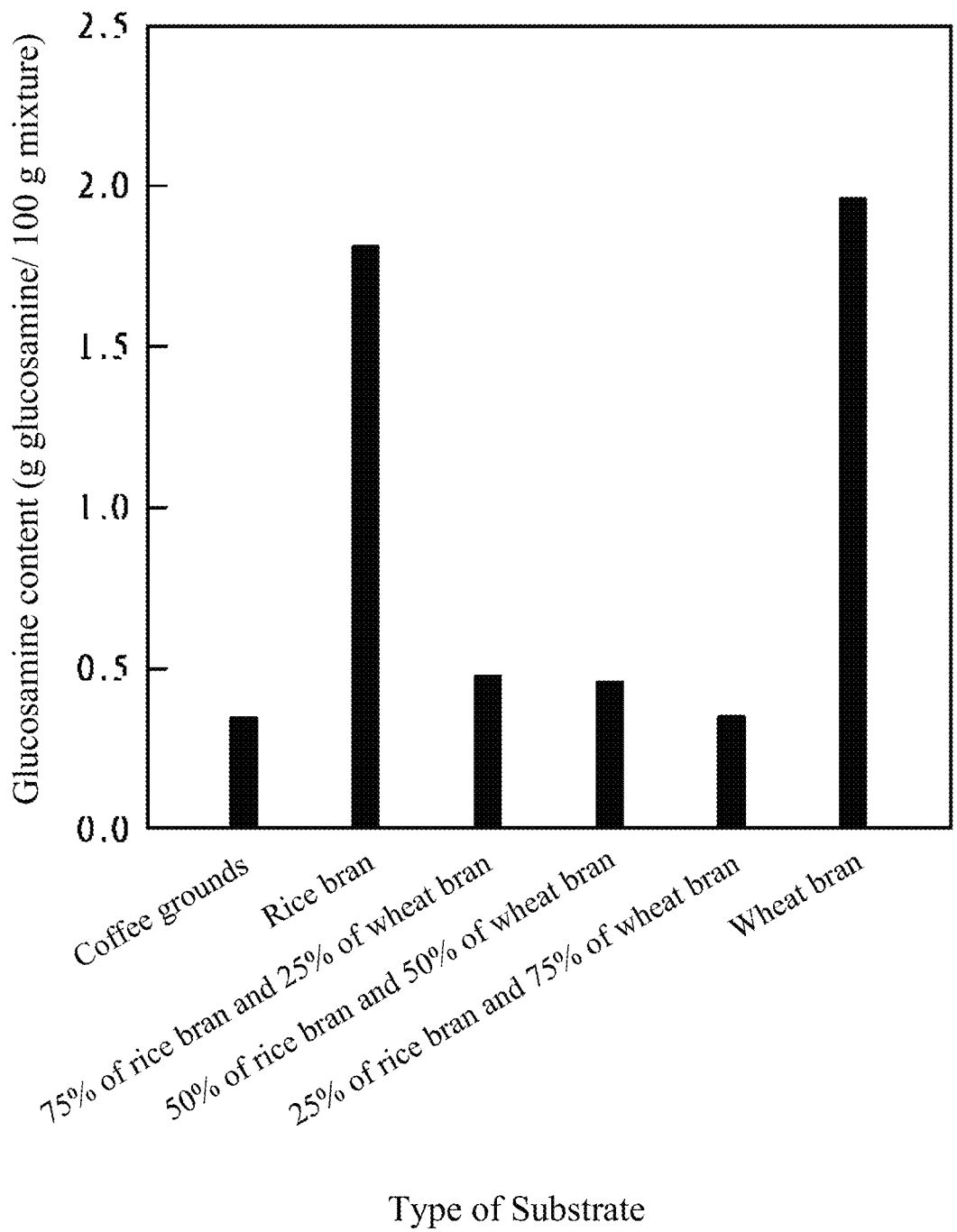
FIG. 1 shows the glucosamine content of *Aspergillus sydowii* BCRC 31742 cultivated in different solid media for three days.

The present invention provides a solid medium for producing glucosamine, comprising substrate and 0.15-4.8 mL/g substrate of supplemental solution, which includes 0.1-2 g/L $KH_2PO_4$, 0.1-2 g/L NaCl, and 0.1-2 g/L $MgSO_4 \cdot 7H_2O$.

The present invention also provides a method for producing glucosamine, comprising:
providing a microorganism being able to produce glucosamine; and
fermenting the microorganism in a solid medium;
wherein the solid medium comprises substrate and 0.15-4.8 mL/g substrate of supplemental solution, which includes 0.1-2 g/L $KH_2PO_4$, 0.1-2 g/L NaCl, and 0.1-2 g/L $MgSO_4 \cdot 7H_2O$.

In some embodiments, the substrate is coffee grounds, and/or rice bran, and/or wheat bran. In some embodiments, the substrate is coffee grounds. In some embodiments, the substrate is rice bran. In some embodiments, the substrate is wheat bran. In some embodiments, the substrate is a mixture of coffee grounds and rice bran. In some embodiments, the substrate is a mixture of coffee grounds and wheat bran. In some embodiments, the substrate is a mixture of rice bran and wheat bran. In some embodiments, the percentages by weight of coffee grounds and rice bran, or the percentages by weight of coffee grounds and wheat bran, or the percentages by weight of rice bran and wheat bran, may be 5 wt % and 95 wt %, 10 wt % and 90 wt %, 15 wt % and 85 wt %, 20 wt % and 80 wt %, 25 wt % and 75 wt %, 30 wt % and 70 wt %, 35 wt % and 65 wt %, 40 wt % and 60 wt %, 45 wt % and 55 wt %, 50 wt % and 50 wt %, 55 wt % and 45 wt %, 60 wt % and 40 wt %, 65 wt % and 35 wt %, 70 wt % and 30 wt %, 75 wt % and 25 wt %, 80 wt % and 20 wt %, 85 wt % and 15 wt %, 90 wt % and 10 wt %, or 95 wt % and 5 wt %, respectively. In some embodiments, the substrate is a mixture of coffee grounds, rice bran, and wheat bran, and the percentages by weight of coffee grounds, rice bran, and wheat bran may be 5 wt %, 5 wt % and 90 wt %, 5 wt %, 10 wt % and 85 wt %, 5 wt %, 15 wt % and 80 wt %, 5 wt %, 20 wt % and 75 wt %, 5 wt %, 25 wt % and 70 wt %, 5 wt %, 30 wt % and 65 wt %, 5 wt %, 35 wt % and 60 wt %, 5 wt %, 40 wt % and 55 wt %, 5 wt %, 45 wt % and 50 wt %, 5 wt %, 50 wt % and 45 wt %, 5 wt %, 55 wt % and 40 wt %, 5 wt %, 60 wt % and 35 wt %, 5 wt %, 65 wt % and 0 wt %, 5 wt %, 70 wt % and 25 wt %, 5 wt %, 75 wt % and 20 wt %, 5 wt %, 80 wt % and 15 wt %, 5 wt %, 85 wt % and 10 wt %, 5 wt %, 90 wt % and 5 wt %, 10 wt %, 5 wt % and 85 wt %, 10 wt %, 10 wt % and 80 wt %, 10 wt %, 15 wt % and 75 wt %, 10 wt %, 20 wt % and 70 wt %, 10 wt %, 25 wt % and 65 wt %, 10 wt %, 30 wt % and 60 wt %, 10 wt %, 35 wt % and 55 wt %, 10 wt %, 40 wt % and 50 wt %, 10 wt %, 45 wt % and 45 wt %, 10 wt %, 50 wt % and 40 wt %, 10 wt %, 55 wt % and 35 wt %, 10 wt %, 60 wt % and 30 wt %, 10 wt %, 65 wt % and 25 wt %, 10 wt %, 70 wt % and 20 wt %, 10 wt %, 75 wt % and 15 wt %, 10 wt %, 80 wt % and 10 wt %, 10 wt %, 85 wt % and 5 wt %, 15 wt %, 5 wt % and 80 wt %, 15 wt %, 10 wt % and 75 wt %, 15 wt %, 15 wt % and 70 wt %, 15 wt %, 20 wt % and 65 wt %, 15 wt %, 25 wt % and 60 wt %, 15 wt %, 30 wt % and 55 wt %, 15 wt %, 35 wt % and 50 wt %, 15 wt %, 40 wt % and 45 wt %, 15 wt %, 45 wt % and 40 wt %, 15 wt %, 50 wt % and 35 wt %, 15 wt %, 55 wt % and 30 wt %, 15 wt %, 60 wt % and 25 wt %, 15 wt %, 65 wt % and 20 wt %, 15 wt %, 70 wt % and 15 wt %, 15 wt %, 75 wt % and 10 wt %, 15 wt %, 80 wt % and 5 wt %, 20 wt %, 5 wt % and 75 wt %, 20 wt %, 10 wt % and 70 wt %, 20 wt %, 15 wt % and 65 wt %, 20 wt %, 20 wt % and 60 wt %, 20 wt %, 25 wt % and 55 wt %, 20 wt %, 30 wt % and 50 wt %, 20 wt %, 35 wt % and 45 wt %, 20 wt %, 40 wt % and 40 wt %, 20 wt %, 45 wt % and 35 wt %, 20 wt %, 50 wt % and 30 wt %, 20 wt %, 55 wt % and 25 wt %, 20 wt %, 60 wt % and 20 wt %, 20 wt %, 65 wt % and 15 wt %, 20 wt %, 70 wt % and 10 wt %, 20 wt %, 75 wt % and 5 wt %, 25 wt %, 5 wt % and 70 wt %, 25 wt %, 10 wt % and 65 wt %, 25 wt %, 15 wt % and 60 wt %, 25 wt %, 20 wt % and 55 wt %, 25 wt %, 25 wt % and 50 wt %, 25 wt %, 30 wt % and 45 wt %, 25 wt %, 35 wt % and 40 wt %, 25 wt %, 40 wt % and 35 wt %, 25 wt %, 45 wt % and 30 wt %, 25 wt %, 50 wt % and 25 wt %, 25 wt %, 55 wt % and 20 wt %, 25 wt %, 60 wt % and 15 wt %, 25 wt %, 65 wt % and 10 wt %, 25 wt %, 70 wt % and 5 wt %, 30 wt %, 5 wt % and 65 wt %, 30 wt %, 10 wt % and 60 wt %, 30 wt %, 15 wt % and 55 wt %, 30 wt %, 20 wt % and 50 wt %, 30 wt %, 25 wt % and 45 wt %, 30 wt %, 30 wt % and 40 wt %, 30 wt %, 35 wt % and 35 wt %, 30 wt %, 40 wt % and 30 wt %, 30 wt %, 45 wt % and 25 wt %, 30 wt %, 50 wt % and 20 wt %, 30 wt %, 55 wt % and 15 wt %, 30 wt %, 60 wt % and 10 wt %, 30 wt %, 65 wt % and 5 wt %, 35 wt %, 5 wt % and 60 wt %, 35 wt %, 10 wt % and 55 wt %, 35 wt %, 15 wt % and 50 wt %, 35 wt %, 20 wt % and 45 wt %, 35 wt %, 25 wt % and 40 wt %, 35 wt %, 30 wt % and 35 wt %, 35 wt %, 35 wt % and 30 wt %, 35 wt %, 40 wt % and 25 wt %, 35 wt %, 45 wt % and 20 wt %, 35 wt %, 50 wt % and 15 wt %, 35 wt %, 55 wt % and 10 wt %, 35 wt %, 60 wt % and 5 wt %, 40 wt %, 5 wt % and 55 wt %, 40 wt %, 10 wt % and 50 wt %, 40 wt %, 15 wt % and 45 wt %, 40 wt %, 20 wt % and 40 wt %, 40 wt %, 25 wt % and 35 wt %, 40 wt %, 30 wt % and 30 wt %, 40 wt %, 35 wt % and 25 wt %, 40 wt %, 40 wt % and 20 wt %, 40 wt %, 45 wt % and 15 wt %, 40 wt %, 50 wt % and 10 wt %, 40 wt %, 55 wt % and 5 wt %, 45 wt %, 5 wt % and 50 wt %, 45 wt %, 10 wt % and 45 wt %, 45 wt %, 15 wt % and 40 wt %, 45 wt %, 20 wt % and 35 wt %, 45 wt %, 25 wt % and 30 wt %, 45 wt %, 30 wt % and 25 wt %, 45 wt %, 35 wt % and 20 wt %, 45 wt %, 40 wt % and 15 wt %, 45 wt %, 45 wt % and 10 wt %, 45 wt %, 50 wt % and 5 wt %, 50 wt %, 5 wt % and 45 wt %, 50 wt %, 10 wt % and 40 wt %, 50 wt %, 15 wt % and 35 wt %, 50 wt %, 20 wt % and 30 wt %, 50 wt %, 25 wt % and 25 wt %, 50 wt %, 30 wt % and 20 wt %, 50 wt %, 35 wt % and 15 wt %, 50 wt %, 40 wt % and 10 wt %, 50 wt %, 45 wt % and 5 wt %, 55 wt %, 5 wt % and 40 wt %, 55 wt %, 10 wt % and 35 wt %, 55 wt %, 15 wt % and 30 wt %, 55 wt %, 20 wt % and 25 wt %, 55 wt %, 25 wt % and 20 wt %, 55 wt %, 30 wt % and 15 wt %, 55 wt %, 35 wt % and 10 wt %, 55 wt %, 40 wt % and 5 wt %, 60 wt %, 5 wt % and 35 wt %, 60 wt %, 10 wt % and 30 wt %, 60 wt %, %, 15 wt % and 25 wt %, 60 wt %, 20 wt % and 20 wt %, 60 wt %, 25 wt % and 15 wt %, 60 wt %, 30 wt % and 10 wt %, 60 wt %, 35 wt % and 5 wt %, 65 wt %, 5 wt % and 30 wt %, 65 wt %, 10 wt % and 25 wt %, 65 wt %, 15 wt % and 20 wt %, 65 wt %, 20 wt % and 15 wt %, 65 wt %, 25 wt % and 10 wt %, 65 wt %, 30 wt % and 5 wt %, 70 wt %, 5 wt % and 25 wt %, 70 wt %, 10 wt % and 20 wt %, 70 wt %, 15 wt % and 15 wt %, 70 wt %, 20 wt % and 10 wt %, 70 wt %, 25 wt % and 5 wt %, 75 wt %, 5 wt % and 20 wt %, 75 wt %, 10 wt % and 15 wt %, 75 wt %, 15 wt % and 10 wt %, 75 wt %, 20 wt % and 5 wt %, 80 wt %, 5 wt % and 15 wt %, 80 wt %, 10 wt % and 10 wt %, 80 wt %, 15 wt % and 5 wt %, 85 wt %, 5 wt % and 10 wt %, 85 wt %, 10 wt % and 5 wt %, or 90 wt %, 5 wt % and 5 wt %, respectively.

In some embodiments, the substrate is treated by high temperature and/or high pressure to release its nutrients or to decompose large molecules into smaller ones. In some preferred embodiments, the substrate is treated by using autoclave at 121° C., saturated steam for 15-20 minutes.

In some embodiments, the substrate is in a container and has a thickness of 0.5-2.5 mm. In some preferred embodiments, the substrate has a thickness of 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 mm in the container.

In some embodiments, the solid medium further comprises 5-50 percentage by volume of molasses. In some preferred embodiments, the percentage of molasses preferably is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 vol %.

In some embodiments, the molasses is pretreated with the following steps: mixing a molasses stock with water at a ratio of 0.5:1 to 5:1 by volume, allowing the mixed molasses stock and water to settle and form an upper layer and a lower layer, and collecting the upper layer as treated molasses. In some preferred embodiments, the molasses stock is mixed with water at a ratio of 0.5:1, 1:1, 1.5:1, 2:1, 2.5:1, 3:1, 3.5:1, 4:1, 4.5:1, or 5:1 by volume.

In some embodiments, the concentration of molasses is 25-500 g/L. In some preferred embodiments, the concentration of molasses is 25, 30, 40, 50, 60, 70, 80, 90, 100, 125, 150, 175, 200, 225, 250, 275, 300, 325, 350, 375, 400, 425, 450, 475, or 500 g/L.

In some embodiments, the concentration of $KH_2PO_4$ is 0.1-2 g/L. In some preferred embodiments, the concentration of $KH_2PO_4$ is 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 g/L.

In some embodiments, the concentration of NaCl is 0.1-2 g/L. In some preferred embodiments, the concentration of NaCl is 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 g/L.

In some embodiments, the concentration of $MgSO_4.7H_2O$ is 0.1-2 g/L. In some preferred embodiments, the concentration of $MgSO_4.7H_2O$ is 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 g/L.

In some embodiments, the microorganism being able to produce glucosamine includes, but not limited to, *Absidia coerulea*, *Aspergillus sydowii*, and *Mucor indicus*.

In some embodiments, the microorganism has an inoculum amount of 9 to 36 mg/g substrate. In some preferred embodiments, the inoculum amount of the microorganism is 9, 10, 11, 12, 13, 14, 15, 16, 17, 18, 19, 20, 21, 22, 23, 25, 26, 27, 28, 29, 30, 31, 32, 33, 34, 35, or 36 mg/g substrate.

In some embodiments, the supplemental solution is divided into a first portion and a second portion, the first portion has 50-60 percentage by volume (vol %) of the supplemental solution, and the second portion has 40-50 vol % of the supplemental solution, and the first portion is added to the substrate before the second portion is added to the substrate. In some preferred embodiments, the first portion has 50, 55, or 60 vol % of the supplemental solution, and the second portion has 40, 45, or 50 vol % of the supplemental solution.

In some embodiments, the microorganism is fermented at 25-50° C. In some preferred embodiments, the microorganism is fermented at 25, 26, 27, 28, 29, 30, 31, 32, 33, 34, 35, 36, 37, 38, 39, 40, 41, 42, 43, 44, 45, 46, 47, 48, 49, or 50° C.

In some embodiments, the microorganism is fermented in an environment of pH 4-9. In some preferred embodiments, the microorganism is fermented in an environment of pH 4, 4.5, 5, 5.5, 6, 6.5, 7, 7.5, 8, 8.5, or 9.

In some embodiments, the microorganism is fermented for 48-120 hours. In some preferred embodiments, the microorganism is fermented for 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours.

In some embodiments, glucosamine is harvested when the microorganism begins to produce spore capsule.

As used herein, the singular forms "a", "an", and "the" include plural referents unless the context clearly dictates otherwise. Thus, for example, reference to "a component" includes a plurality of such components and equivalents thereof known to those skilled in the art. Moreover, titles or subtitles may be used in the specification for the convenience of a reader, which shall have no influence on the scope of the present invention.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "high temperature" refers to a temperature higher than room temperature. In some embodiments, high temperature refers to a temperature higher than 42° C.

As used herein, the term "high pressure" refers to a pressure higher than the standard atmosphere, i.e., higher than about 1.033 $kg/cm^2$.

The meaning of the technical and scientific terms as described herein can be clearly understood by a person of ordinary skill in the art.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views.

Example 1

Effects of Different Solid Medium on Fungal Growth

In this Example, coffee grounds, rice bran, and wheat bran are used as substrate of solid medium to test their effects on fungal growth.

I. Fungal Fermentation Test

*A. sydowii* BCRC 31742 (Hsinchu, Taiwan) was used in this Example. First, the fungi were recovered by being subcultured twice with the following method. *A. sydowii* BCRC 31742 was first cultured on Potato Dextrose Agar (PDA) [4 g/L Potato Dextrose Broth (PDB) and 15 g/L Agar] by the three-sector streaking method to obtain isolated colonies at 30° C. for 3 days. An isolated colony of *A. sydowii* BCRC 31742 was then seeded in a 250 mL flask containing 150 mL of sterilized $M_{150}Sb_5AlMe$ liquid medium (150 mL/L treated molasses (equivalent to about 207 g/L), 5 mL/L soybean hydrolysate, 0.1 g/L $MgSO_4.7H_2O$, 0.1 g/L $Al(NO_3)_3$, and 0.8 g/L methanol) and incubated at 30° C., 200 rpm for 5 days.

After that, 6 mL of the recovered fungi were seeded on different glass petri dishes with a diameter of 9 cm containing the following media, respectively:

(1) Coffee grounds solid medium [5 g sterilized coffee grounds and 15 mL supplemental solution (equivalent to 3 mL/g substrate) containing 0.2 wt % $KH_2PO_4$, 0.1 wt % NaCl, and 0.1 wt % $MgSO_4.7H_2O$];

(2) Rice bran solid medium [5 g sterilized rice bran and 15 mL supplemental solution (equivalent to 3 mL/g substrate) containing 0.2 wt % $KH_2PO_4$, 0.1 wt % NaCl, and 0.1 wt % $MgSO_4.7H_2O$];

(3) 75% rice bran and 25% wheat bran solid medium [3.75 g sterilized rice bran, 1.25 g sterilized wheat bran, and 15 mL supplemental solution (equivalent to 3 mL/g substrate) containing 0.2 wt % $KH_2PO_4$, 0.1 wt % NaCl, and 0.1 wt % $MgSO_4.7H_2O$];

(4) 50% rice bran and 50% wheat bran solid medium [2.5 g sterilized rice bran, 2.5 g sterilized wheat bran, and 15 mL supplemental solution (equivalent to 3 mL/g substrate) containing 0.2 wt % $KH_2PO_4$, 0.1 wt % NaCl, and 0.1 wt % $MgSO_4.7H_2O$];

(5) 25% rice bran and 75% wheat bran solid medium [1.25 g sterilized rice bran, 3.75 g sterilized wheat bran, and 15 mL supplemental solution (equivalent to 3 mL/g substrate) containing 0.2 wt % $KH_2PO_4$, 0.1 wt % NaCl, and 0.1 wt % $MgSO_4. 7H_2O$];

(6) Wheat bran solid medium [5 g sterilized wheat bran and 15 mL supplemental solution (equivalent to 3 mL/g substrate) containing 0.2 wt % $KH_2PO_4$, 0.1 wt % NaCl, and 0.1 wt % $MgSO_4.7H_2O$].

The fungi were incubated at 30° C. for 3 days, and then were subject to determination of glucosamine.

II. Determination of Glucosamine

After the fungi were incubated for 3 days, the mixture of cells and the substrate was collected and dried at 60° C. to a constant weight. The weight of the substrate was subtracted from the constant weight to obtain the weight of biomass. The dried mixture was homogenized by a blender, and then 1 gram of the dried mixture was mixed with 10 mL of 6N HCl and incubated at a 100° C. oven for 4 hours to obtain a liquid containing glucosamine. After the mixture was cooled to room temperature, 10 mL of deionized water was added, and the diluted mixture was neutralized to pH 7 with 10 N NaOH and then vacuum filtered to collect the filtrate. Zero point two (0.2) milliliter of the filtrate, 0.2 mL of 3,5-Dinitrobenzonitrile acetonitrile as the internal standard, and 0.6 mL of 40 mol/m³ 1-naphthyl isothiocyanate pyridine were mixed in a test tube and incubated at 50° C. in a shaking water bath for 1 hour. After that, 5 μL of the mixture was taken for determination of glucosamine.

High performance liquid chromatography (HPLC) was used to determine glucosamine. Conditions of HPLC are shown as follows.

HPLC pump: Shimadzu LC-20A;
Detector: Shimadzu Model SPD-10A UV-VIS index detector;
Column: Merck Purospher® STAR Rp-18 endcapped (5 μm), 250×4 mm I.D.;
Mobile phase: Water/Acetonitrile (85/15);
Flow rate: 1.1 mL/min; and
Wavelength of UV detector: 230 nm.

The amount of glucosamine in the test sample was calculated by the following method. First, a calibration curve of glucosamine hydrochloride was created based on weight ratios and peak area ratios of glucosamine to different concentrations of the internal standard. Then, the peak area ratio of the glucosamine hydrochloride in the test sample to the internal standard in the test sample was substituted in the calibration curve to obtain the amount of glucosamine by interpolation method. Glucosamine content (gram of glucosamine/100 g mixture) was calculated based on the obtained amounts of glucosamine. The results are shown in FIG. 1. The results indicate that *A. sydowii* is able to grow on each of coffee grounds, rice bran, wheat bran, and mixture of rice bran and wheat bran and to produce glucosamine. *A. sydowii* growing on wheat bran and rice bran have the highest and the second highest content of glucosamine among other substrate.

III. Analysis of Constituents of Wheat Bran

Analyses of constituents of wheat bran were performed by Super Laboratory Co., Ltd. (New Taipei City, Taiwan). Comparison of constituents of wheat bran and molasses stock (a carbon source) and comparison of constituents of wheat bran and soybean hydrolysate (a nitrogen source) are shown in Table 1 and Table 2, respectively.

TABLE 1

Comparison of constituents of wheat bran and molasses stock.

| Items | Unit | Wheat bran | Molasses Stock |
|---|---|---|---|
| Calories | Kcal/100 g | 363.4 | 278.9 |
| Crude Protein | g/100 g | 17.1 | 6.8 |
| Fats | g/100 g | 5.8 | 0.7 |
| Saturated Fat | g/100 g | 0.87 | 0.06 |
| Trans Fat | g/100 g | — | — |
| Carbohydrates | g/100 g | 60.7 | 61.3 |
| Sugar | g/100 g | 2.949 | 39.114 |
| Fructose | g/100 g | 0.862 | 6.682 |
| Glucose | g/100 g | 0.422 | 2.435 |
| Sucrose | g/100 g | 1.665 | 29.653 |
| Maltose | g/100 g | — | 0.289 |
| Lactose | g/100 g | — | 0.055 |
| Metal Ions | | | |
| Sodium | mg/100 g | 9.8 | 70.2 |
| Potassium | mg/100 g | — | 25914.8 |
| Iron | mg/100 g | — | 205.3 |
| Magnesium | mg/100 g | — | 3804.67 |
| Phosphorus | mg/100 g | — | 501.7 |

The results in Table 1 indicate that wheat bran has more large molecules, such as crude protein and fats, as compared to molasses stock. Therefore, after wheat bran is treated by high temperature and/or high pressure, more small molecules will be decomposed from large molecules, and more nutrients in wheat bran will be released, which is beneficial to fungus growth, as compared to molasses stock. In addition, although wheat bran has less sugar than molasses stock, wheat bran and molasses stock have similar content of carbohydrates, which means wheat bran provides enough carbon source for fungal growth without addition of sugar.

TABLE 2

Analyses of amino acid composition of wheat bran and soybean hydrolysate

| Items | Unit | Wheat bran | Soybean Hydrolysate |
|---|---|---|---|
| Alanine | mg/100 g | 823.3 | 23.96 |
| Glycine | mg/100 g | 903.0 | 23.52 |
| Valine | mg/100 g | 823.3 | 23.85 |
| Leucine | mg/100 g | 977.9 | 43.78 |
| Isoleucine | mg/100 g | 544.4 | 24.36 |
| Proline | mg/100 g | 797.9 | 30.07 |
| Glutamic acid | mg/100 g | 3355.0 | 109.09 |
| Methionine | mg/100 g | 75.0 | 7.42 |
| Asparagine | mg/100 g | 1182.8 | 65.14 |
| Hydroxyproline | mg/100 g | 974.2 | — |
| Phenylalanine | mg/100 g | 607.4 | 27.62 |
| Cysteine | mg/100 g | 125.0 | 6.81 |
| Lysine | mg/100 g | 727.0 | 34.18 |
| Histidine | mg/100 g | 367.5 | 14.22 |
| Tyrosine | mg/100 g | 261.3 | 21.36 |
| Serine | mg/100 g | 422.2 | 29.38 |
| Threonine | mg/100 g | 377.3 | 21.99 |

The results in Table 2 show that wheat bran has 10 times more amino acid content than soybean hydrolysate. Therefore, wheat bran provides enough nitrogen source for fungal growth without addition of other nitrogen source.

Example 2

Cultivation of Different Fungi on Solid Medium

I. Fungal Fermentation Test

*A. sydowii* BCRC 31742, *Rhizomucor pusillus* BCRC33122, and *Gongronella butleri*, BCRC 31348 were all purchased from Bioresource Collection and Research Center, Food Industry Research and Development Institute (Hsinchu, Taiwan) and used in the tests of this Example. First, the fungi were recovered by being subcultured twice with the method described in Example 1.

After that, 6 mL of the recovered fungi were seeded on glass petri dishes with a diameter of 9 cm containing wheat bran solid medium [5 g sterilized wheat bran and 15 mL supplemental solution (equivalent to 3 mL/g substrate) containing 0.2 wt % $KH_2PO_4$, 0.1 wt % NaCl, and 0.1 wt % $MgSO_4.7H_2O$]. The fungi were incubated at 30° C. for 3 days, and then were subject to determination of glucosamine.

II. Determination of Glucosamine

Figure 2:
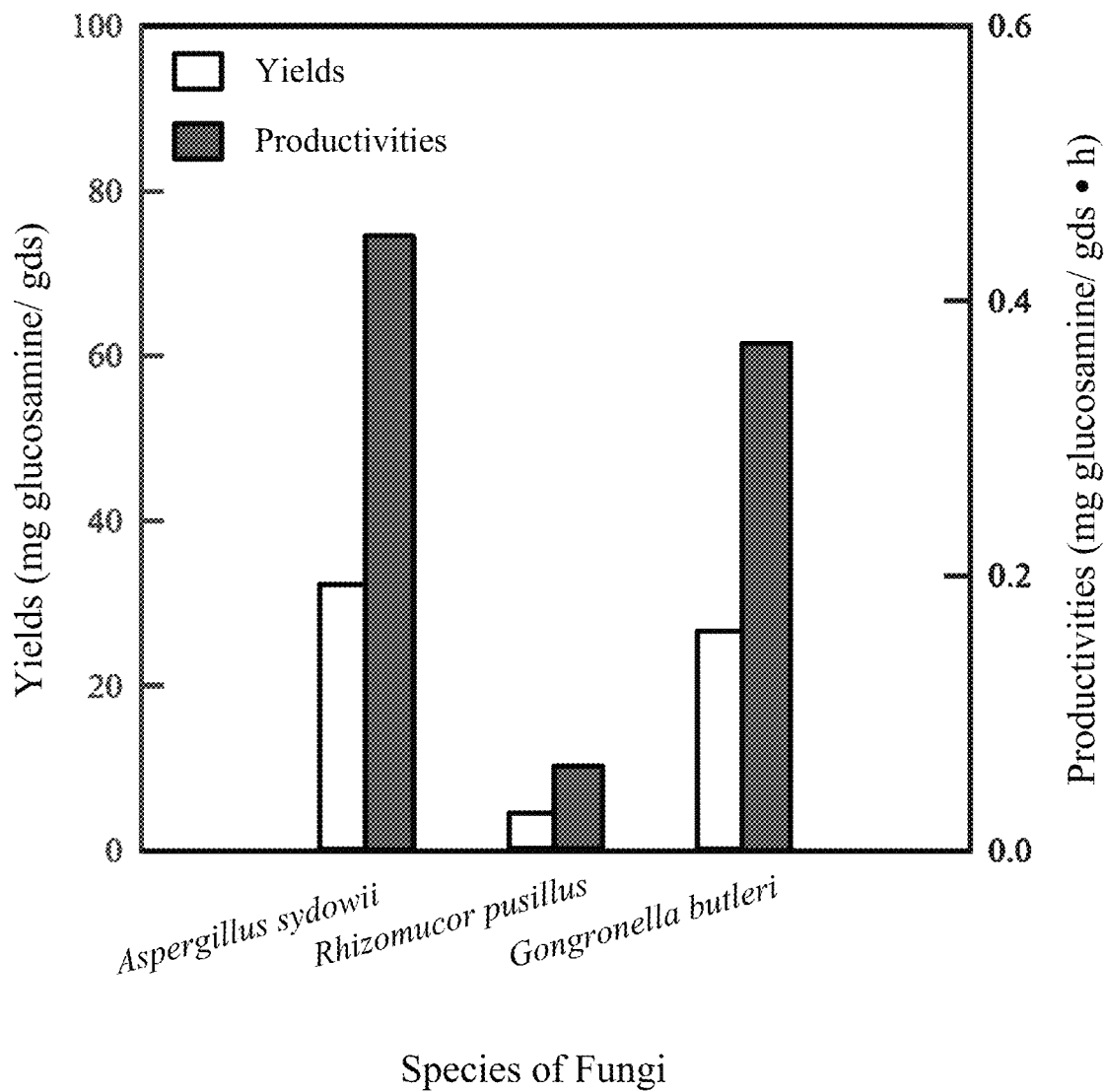
FIG. 2 shows the yields and productivities of glucosamine produced by *A. sydowii* BCRC 31742, *Rhizomucor pusillus* BCRC33122, and *Gongronella butleri* BCRC 31348 cultivated in a solid medium containing wheat bran for three days.

Treatment of the fungi and analysis method and conditions of HPLC are the same as those described in Example 1. Yield is calculated by dividing the amount of glucosamine obtained by the weight of dry substrate. Productivity is calculated by dividing the amount of the obtained glucosamine by the weight of dry substrate and incubation time. The results of yields and productivities of glucosamine produced by *A. sydowii*, *R. pusillus*, and *G. butleri* are shown in FIG. 2.

In this Example, all of the three fungi, *A. sydowii*, *R. pusillus*, and *G. butleri*, are proved to be able to grow on the wheat bran solid medium of the present invention and produce glucosamine. Among all the fungi, *A. sydowii* has the highest yields and productivities of glucosamine.

Example 3

Effects of Volume of Supplemental Solution on Fungal Growth

I. Fungal Fermentation Test

*A. sydowii* BCRC 31742 (Hsinchu, Taiwan) was also used in the tests of this Example. First, the fungi were recovered by being subcultured twice with the method described in Example 1.

After that, 6 mL of the recovered fungi were seeded on different glass petri dishes with a diameter of 9 cm containing the following media, respectively:

(1) Wheat bran solid medium [5 g sterilized wheat bran and 0 mL supplemental solution (equivalent to 0 mL/g substrate)];

(2) Wheat bran solid medium [5 g sterilized wheat bran and 0.75 mL supplemental solution (equivalent to 0.15 mL/g substrate) containing 0.2 wt % $KH_2PO_4$, 0.1 wt % NaCl, and 0.1 wt % $MgSO_4.7H_2O$];

(3) Wheat bran solid medium [5 g sterilized wheat bran and 1.5 mL supplemental solution (equivalent to 0.3 mL/g substrate) containing 0.2 wt % $KH_2PO_4$, 0.1 wt % NaCl, and 0.1 wt % $MgSO_4.7H_2O$];

(4) Wheat bran solid medium [5 g sterilized wheat bran and 3 mL supplemental solution (equivalent to 0.6 mL/g substrate) containing 0.2 wt % $KH_2PO_4$, 0.1 wt % NaCl, and 0.1 wt % $MgSO_4.7H_2O$];

(5) Wheat bran solid medium [5 g sterilized wheat bran and 4.5 mL supplemental solution (equivalent to 0.9 mL/g substrate) containing 0.2 wt % $KH_2PO_4$, 0.1 wt % NaCl, and 0.1 wt % $MgSO_4.7H_2O$];

(6) Wheat bran solid medium [5 g sterilized wheat bran and 6 mL supplemental solution (equivalent to 1.2 mL/g substrate) containing 0.2 wt % $KH_2PO_4$, 0.1 wt % NaCl, and 0.1 wt % $MgSO_4.7H_2O$];

(7) Wheat bran solid medium [5 g sterilized wheat bran and 9 mL supplemental solution (equivalent to 1.8 mL/g substrate) containing 0.2 wt % $KH_2PO_4$, 0.1 wt % NaCl, and 0.1 wt % $MgSO_4.7H_2O$];

(8) Wheat bran solid medium [5 g sterilized wheat bran and 12 mL supplemental solution (equivalent to 2.4 mL/g substrate) containing 0.2 wt % $KH_2PO_4$, 0.1 wt % NaCl, and 0.1 wt % $MgSO_4.7H_2O$];

(9) Wheat bran solid medium [5 g sterilized wheat bran and 13.5 mL supplemental solution (equivalent to 2.7 mL/g substrate) containing 0.2 wt % $KH_2PO_4$, 0.1 wt % NaCl, and 0.1 wt % $MgSO_4.7H_2O$];

(10) Wheat bran solid medium [5 g sterilized wheat bran and 15 mL supplemental solution (equivalent to 3.0 mL/g substrate) containing 0.2 wt % $KH_2PO_4$, 0.1 wt % NaCl, and 0.1 wt % $MgSO_4.7H_2O$];

(11) Wheat bran solid medium [5 g sterilized wheat bran and 16.5 mL supplemental solution (equivalent to 3.3 mL/g substrate) containing 0.2 wt % $KH_2PO_4$, 0.1 wt % NaCl, and 0.1 wt % $MgSO_4.7H_2O$];

(12) Wheat bran solid medium [5 g sterilized wheat bran and 18 mL supplemental solution (equivalent to 3.6 mL/g substrate) containing 0.2 wt % $KH_2PO_4$, 0.1 wt % NaCl, and 0.1 wt % $MgSO_4.7H_2O$];

(13) Wheat bran solid medium [5 g sterilized wheat bran and 19.5 mL supplemental solution (equivalent to 3.9 mL/g substrate) containing 0.2 wt % $KH_2PO_4$, 0.1 wt % NaCl, and 0.1 wt % $MgSO_4.7H_2O$];

(14) Wheat bran solid medium [5 g sterilized wheat bran and 21 mL supplemental solution (equivalent to 4.2 mL/g substrate) containing 0.2 wt % $KH_2PO_4$, 0.1 wt % NaCl, and 0.1 wt % $MgSO_4.7H_2O$];

(15) Wheat bran solid medium [5 g sterilized wheat bran and 22.5 mL supplemental solution (equivalent to 4.5 mL/g substrate) containing 0.2 wt % $KH_2PO_4$, 0.1 wt % NaCl, and 0.1 wt % $MgSO_4.7H_2O$]; and

(16) Wheat bran solid medium [5 g sterilized wheat bran and 24 mL supplemental solution (equivalent to 4.8 mL/g substrate) containing 0.2 wt % $KH_2PO_4$, 0.1 wt % NaCl, and 0.1 wt % $MgSO_4.7H_2O$].

The fungi were incubated at 30° C. for 3 days, and then were subject to determination of glucosamine.

II. Determination of Glucosamine

Figure 3:
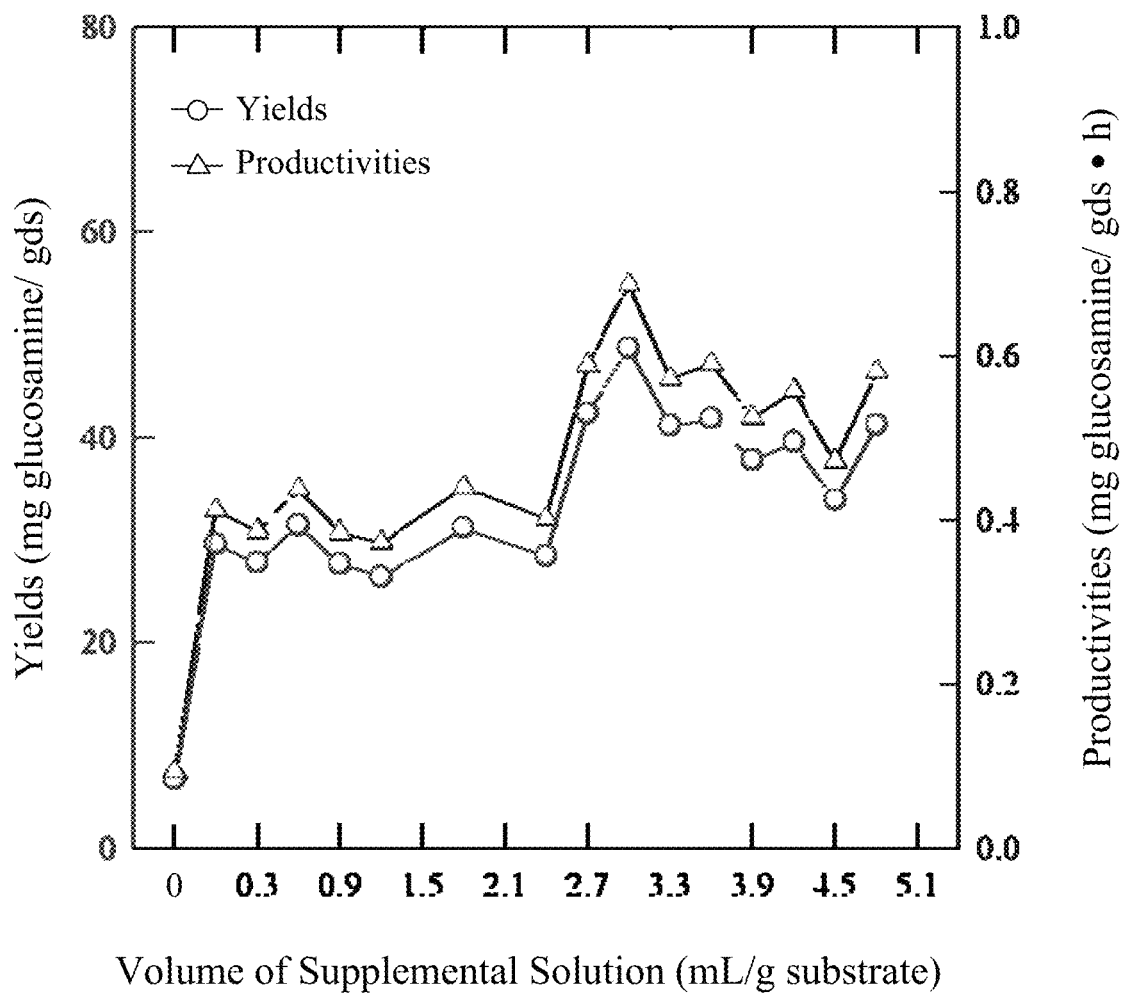
FIG. 3 shows the yields and productivities of glucosamine produced by *A. sydowii* BCRC 31742 cultivated in a solid medium containing wheat bran and different volumes of supplemental solution for three days.

Treatment of the fungi and analysis method and conditions of HPLC are the same as those described in Example 1. Yield is calculated by dividing the amount of glucosamine obtained by the weight of dry substrate. Productivity is calculated by dividing the amount of the obtained glucosamine by the weight of dry substrate and incubation time. The results of yields and productivities of glucosamine produced by *A. sydowii* are shown in FIG. 3.

In this Example, addition of 0.15-4.8 mL/g substrate of supplemental solution is proved to increase yields of glucosamine. The fungi grown on wheat bran solid medium with 3.0 mL/g substrate of supplemental solution have the highest yields and productivities.

Example 4

Effects of Cultivation Time on Fungal Growth

I. Fungal Fermentation Test

*A. sydowii* BCRC 31742 (Hsinchu, Taiwan) was also used in the tests of this Example. First, the fungi were recovered by being subcultured twice with the method described in Example 1.

After that, 6 mL of the recovered fungi were seeded on glass petri dishes with a diameter of 9 cm containing wheat bran solid medium [5 g sterilized wheat bran and 15 mL supplemental solution (equivalent to 3 mL/g substrate) containing 0.2 wt % $KH_2PO_4$, 0.1 wt % NaCl, and 0.1 wt % $MgSO_4.7H_2O$]. The fungi were incubated at 30° C. for 23, 48, 63, 70, 71, 95, 112, 700, and 754 hours, and then were subject to determination of glucosamine.

II. Determination of Glucosamine

Treatment of the fungi and analysis method and conditions of HPLC are the same as those described in Example 1. Yield is calculated by dividing the amount of glucosamine obtained by the weight of dry substrate. Productivity is calculated by dividing the amount of the obtained glucosamine by the weight of dry substrate and incubation time. The results of yields and productivities of glucosamine produced by *A. sydowii* are shown in FIG. 4.

Figure 4:
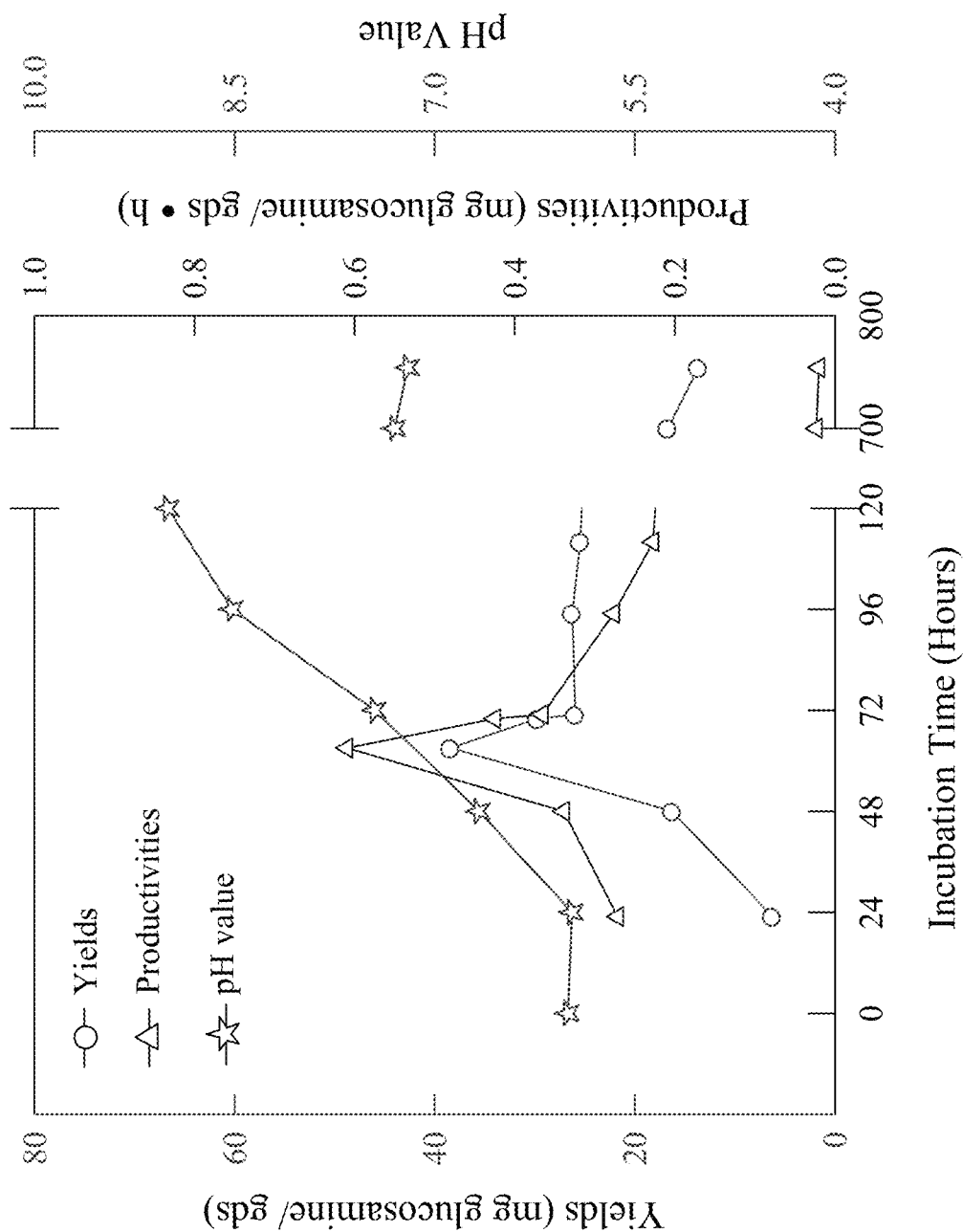
FIG. 4 shows the yields and productivities of glucosamine produced by *A. sydowii* BCRC 31742 cultivated in a solid medium containing wheat bran for different incubation time.
Figure 5A:
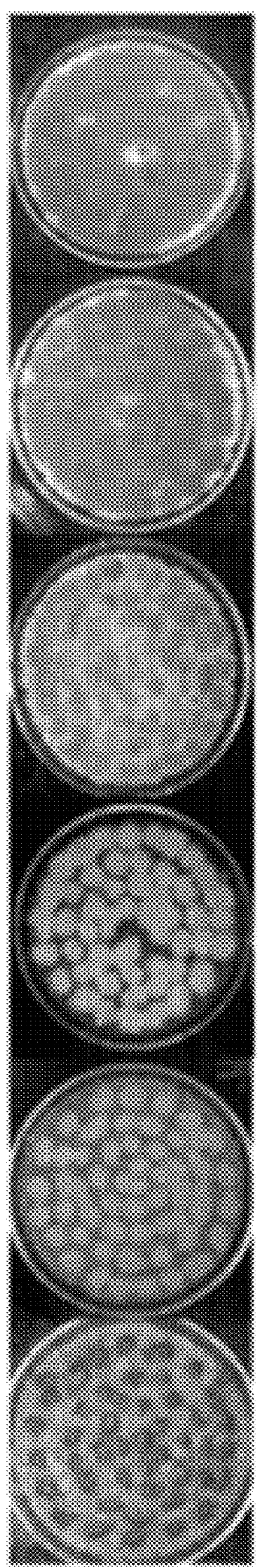
FIG. 5A shows morphology of fungal growth at macro state in a solid medium containing wheat bran for different incubation time.
Figure 5B:
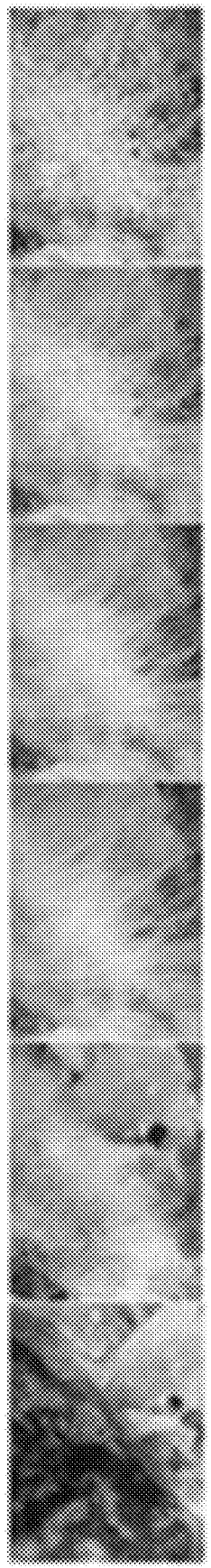
FIG. 5B shows morphology of fungal growth under the microscope (×450) in a solid medium containing wheat bran for different incubation time.

In this Example, fungi cultivated for about 3 days (63, 70, 71 hours) have higher productivities of glucosamine, and the pH value of the solid media at these time points are around 7.0 (FIG. 4). Morphology of fungal growth at both macro state (FIG. 5A) and under the microscope (FIG. 5B) indicates that fungi begin to produce spore capsule at around 3 days of cultivation, which is the same time of highest glucosamine productivities. Therefore, glucosamine is harvested preferably when the fungi begin to produce spore capsule, and the cultivation time of fungi for producing glucosamine is preferably 2 to 5 days, and more preferably 3 days.

In addition, the highest yield, productivity, and production cost of glucosamine produced by *A. sydowii* cultivated in 5 g sterilized wheat bran with 15 mL supplemental solution (equivalent to 3 mL/g substrate) containing 0.2 wt % $KH_2PO_4$, 0.1 wt % NaCl, and 0.1 wt % $MgSO_4.7H_2O$ are 48.7 mg/gds, 0.69 mg/gds·h, and 2 USD/Kg, respectively. Comparison of yields, productivities, and production costs of glucosamine produced by *A. sydowii* cultivated with different methods are shown in Table 3. The results indicate that glucosamine production with the wheat bran solid medium of the present invention has the lowest production cost, which is beneficial to industrial production of glucosamine.

TABLE 3

Comparison of yields, productivities, and production costs of glucosamine

| Medium | Cultivation Method | Yield of Glucosamine | Productivity of Glucosamine | Production cost (USD/kg glucosamine) |
|---|---|---|---|---|
| 5 g wheat bran solid medium | Solid medium cultivation | 48.7 mg/gds | 0.69 mg/gds · h | 2 |
| $M_{300}Sb_5AlMe$* | Shake flask cultivation | 2.63 g/g biomass | 15.6 g/L · h | 11.4 |
| $M_{300}Sb_5AlMe$* | Fermenter | 0.172 g/g biomass | 74.7 g/L · h | 4.2 |

*$M_{300}Sb_5AlMe$ liquid medium contains 300 mL/L molasses (equivalent to about 163 g/L molasses), 5 mL/L soybean hydrolysate (equivalent to about 2.81 g/L soybean hydrolysate), 0.1 g/L $MgSO_4•7H_2O$, 0.1 g/L $Al(NO_3)_3$, 1 mL/L methanol, pH 7.

Example 5

Effects of Inoculum Amount on Fungal Growth

I. Fungal Fermentation Test

*A. sydowii* BCRC 31742 (Hsinchu, Taiwan) was also used in the tests of this Example. First, the fungi were recovered by being subcultured twice with the method described in Example 1.

After that, 3, 6, 9, 12, 15, 18, and 21 mL of the recovered fungi (15±2 mg biomass/mL inoculum) were seeded on glass petri dishes with a diameter of 9 cm containing wheat bran solid medium [5 g sterilized wheat bran and 15 mL supplemental solution (equivalent to 3 mL/g substrate) containing 0.2 wt % $KH_2PO_4$, 0.1 wt % NaCl, and 0.1 wt % $MgSO_4.7H_2O$], respectively. The volume of each inoculum is 0.6, 1.2, 1.8, 2.4, 3.0, 3.6 and 4.2 mL/g substrate, and the biomass of each inoculum is 9, 18, 27, 36, 45, 54, and 63 mg/g substrate. The fungi were incubated at 30° C. for 3 days, and then were subject to determination of glucosamine.

II. Determination of Glucosamine

Figure 6:
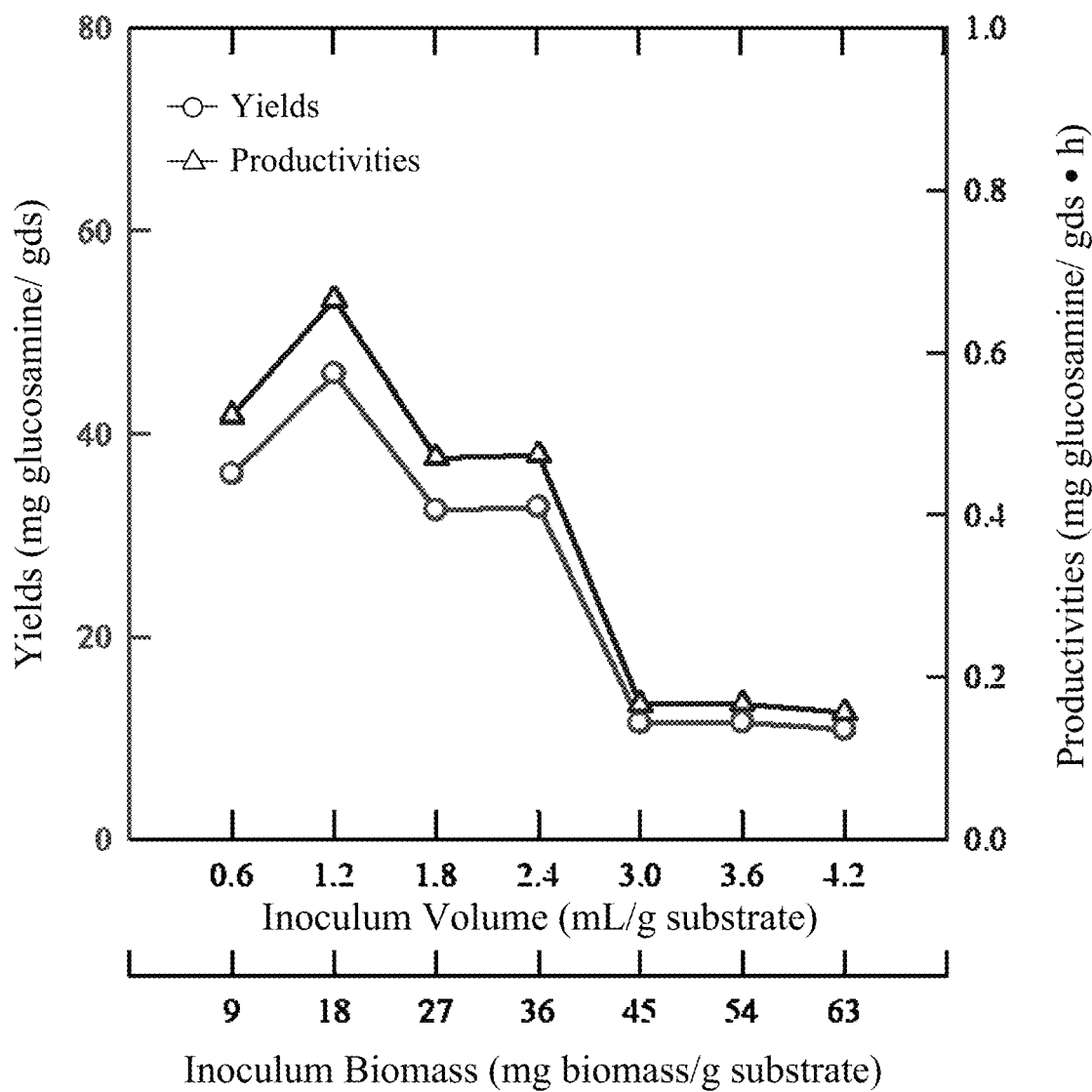
FIG. 6 shows the yields and productivities of glucosamine produced by *A. sydowii* BCRC 31742 cultivated in a solid medium containing wheat bran with different amount of inoculum biomass for three days.

Treatment of the fungi and analysis method and conditions of HPLC are the same as those described in Example 1. Yield is calculated by dividing the amount of glucosamine obtained by the weight of dry substrate. Productivity is calculated by dividing the amount of the obtained glucosamine by the weight of dry substrate and incubation time. The results of yields and productivities of glucosamine produced by *A. sydowii* are shown in FIG. 6.

In this Example, fungi cultivated with 1.2 mL inoculum/g substrate (equivalent to 18 mg biomass/g substrate) have the highest productivity of glucosamine. Therefore, in view of glucosamine productivity, the inoculum amount of fungi is preferably 0.6-2.4 mL/g substrate (equivalent to 9-36 mg biomass/g substrate), more preferably 1.2 mL/g substrate (equivalent to 18 mg biomass/g substrate).

Example 6

Effects of Medium Thickness on Fungal Growth

I. Fungal Fermentation Test

*A. sydowii* BCRC 31742 (Hsinchu, Taiwan) was also used in the tests of this Example. First, the fungi were recovered by being subcultured twice with the method described in Example 1.

After that, 1.2 mL/g substrate of the recovered fungi (15±2 mg biomass/mL inoculum) were seeded on different glass petri dishes with a diameter of 9 cm containing the following media, respectively:

(1) Wheat bran solid medium with 1.0 mm thickness [2 g sterilized wheat bran and 6 mL supplemental solution (equivalent to 3 mL/g substrate) containing 0.2 wt % $KH_2PO_4$, 0.1 wt % NaCl, and 0.1 wt % $MgSO_4.7H_2O$];

(2) Wheat bran solid medium with 1.6 mm thickness [3 g sterilized wheat bran and 9 mL supplemental solution (equivalent to 3 mL/g substrate) containing 0.2 wt % $KH_2PO_4$, 0.1 wt % NaCl, and 0.1 wt % $MgSO_4.7H_2O$];

(3) Wheat bran solid medium with 2.2 mm thickness [4 g sterilized wheat bran and 12 mL supplemental solution (equivalent to 3 mL/g substrate) containing 0.2 wt % $KH_2PO_4$, 0.1 wt % NaCl, and 0.1 wt % $MgSO_4.7H_2O$];

(4) Wheat bran solid medium with 2.4 mm thickness [5 g sterilized wheat bran and 15 mL supplemental solution (equivalent to 3 mL/g substrate) containing 0.2 wt % $KH_2PO_4$, 0.1 wt % NaCl, and 0.1 wt % $MgSO_4.7H_2O$]; and (5) Wheat bran solid medium with 2.9 mm thickness [6 g sterilized wheat bran and 18 mL supplemental solution (equivalent to 3 mL/g substrate) containing 0.2 wt % $KH_2PO_4$, 0.1 wt % NaCl, and 0.1 wt % $MgSO_4.7H_2O$].

The fungi were incubated at 30° C. for 3 days, and then were subject to determination of glucosamine.

II. Determination of Glucosamine

Figure 7:
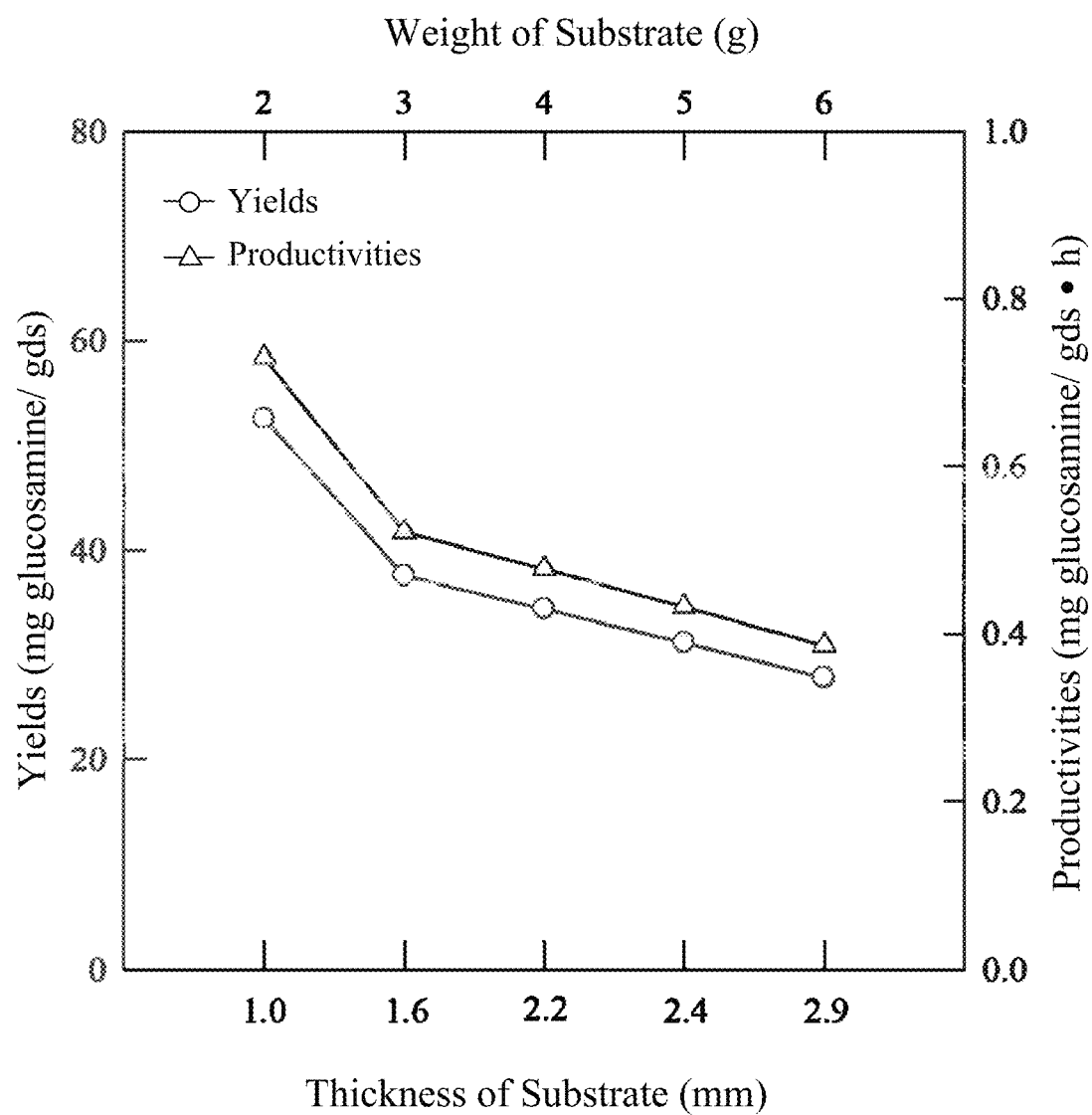
FIG. 7 shows the yields and productivities of glucosamine produced by *A. sydowii* BCRC 31742 cultivated in a solid medium containing wheat bran with different thickness of the solid medium for three days.

Treatment of the fungi and analysis method and conditions of HPLC are the same as those described in Example 1. Yield is calculated by dividing the amount of glucosamine obtained by the weight of dry substrate. Productivity is calculated by dividing the amount of the obtained glucosamine by the weight of dry substrate and incubation time. The results of yields and productivities of glucosamine produced by *A. sydowii* are shown in FIG. 7.

In this Example, fungi cultivated in the solid medium with 1.0 mm thickness (2 g wheat bran) have the highest yield and productivity of glucosamine, which is 52.5 mg/gds and 0.73 mg/gds·h, respectively. Therefore, in view of glucosamine productivity, the thickness of solid medium is preferably 1.0-2.4 mm, more preferably 1.0 mm.

Example 7

Effects of Different Amounts of Molasses on Fungal Growth

I. Fungal Fermentation Test

Molasses stock was mixed with water at a ratio of 1:1 by volume, and the mixture was stirred until molasses stock was completely dissolved. The mixture was then stored at 4° C. to settle until two layers were formed. The upper layer was collected as treated molasses.

*A. sydowii* BCRC 31742 (Hsinchu, Taiwan) was also used in the tests of this Example. First, the fungi were recovered by being subcultured twice with the method described in Example 1.

After that, 1.2 mL/g substrate of the recovered fungi (15±2 mg biomass/mL inoculum) were seeded on different glass petri dishes with a diameter of 9 cm containing the following media, respectively:

(1) Wheat bran solid medium without molasses [5 g sterilized wheat bran and 15 mL supplemental solution (equivalent to 3 mL/g substrate) containing 0.2 wt % $KH_2PO_4$, 0.1 wt % NaCl, and 0.1 wt % $MgSO_4.7H_2O$];

(2) Wheat bran solid medium with 10 vol % of molasses [5 g sterilized wheat bran and 15 mL supplemental solution with 10 vol % of molasses (equivalent to 3 mL/g substrate) containing 0.2 wt % $KH_2PO_4$, 0.1 wt % NaCl, 0.1 wt % $MgSO_4.7H_2O$, and 1.5 mL treated molasses];

(3) Wheat bran solid medium with 20 vol % of molasses [5 g sterilized wheat bran and 15 mL supplemental solution with 20 vol % of molasses (equivalent to 3 mL/g substrate) containing 0.2 wt % $KH_2PO_4$, 0.1 wt % NaCl, 0.1 wt % $MgSO_4.7H_2O$, and 3 mL treated molasses];

(4) Wheat bran solid medium with 30 vol % of molasses [5 g sterilized wheat bran and 15 mL supplemental solution with 30 vol % of molasses (equivalent to 3 mL/g substrate) containing 0.2 wt % $KH_2PO_4$, 0.1 wt % NaCl, 0.1 wt % $MgSO_4.7H_2O$, and 4.5 mL treated molasses];

(5) Wheat bran solid medium with 40 vol % of molasses [5 g sterilized wheat bran and 15 mL supplemental solution with 40 vol % of molasses (equivalent to 3 mL/g substrate) containing 0.2 wt % $KH_2PO_4$, 0.1 wt % NaCl, 0.1 wt % $MgSO_4.7H_2O$, and 6 mL treated molasses]; and (6) Wheat bran solid medium with 50 vol % of molasses [5 g sterilized wheat bran and 15 mL supplemental solution with 50 vol % of molasses (equivalent to 3 mL/g substrate) containing 0.2 wt % $KH_2PO_4$, 0.1 wt % NaCl, 0.1 wt % $MgSO_4.7H_2O$, and 7.5 mL treated molasses].

The fungi were incubated at 30° C. for 3 days, and then were subject to determination of glucosamine.

II. Determination of Glucosamine

Figure 8:
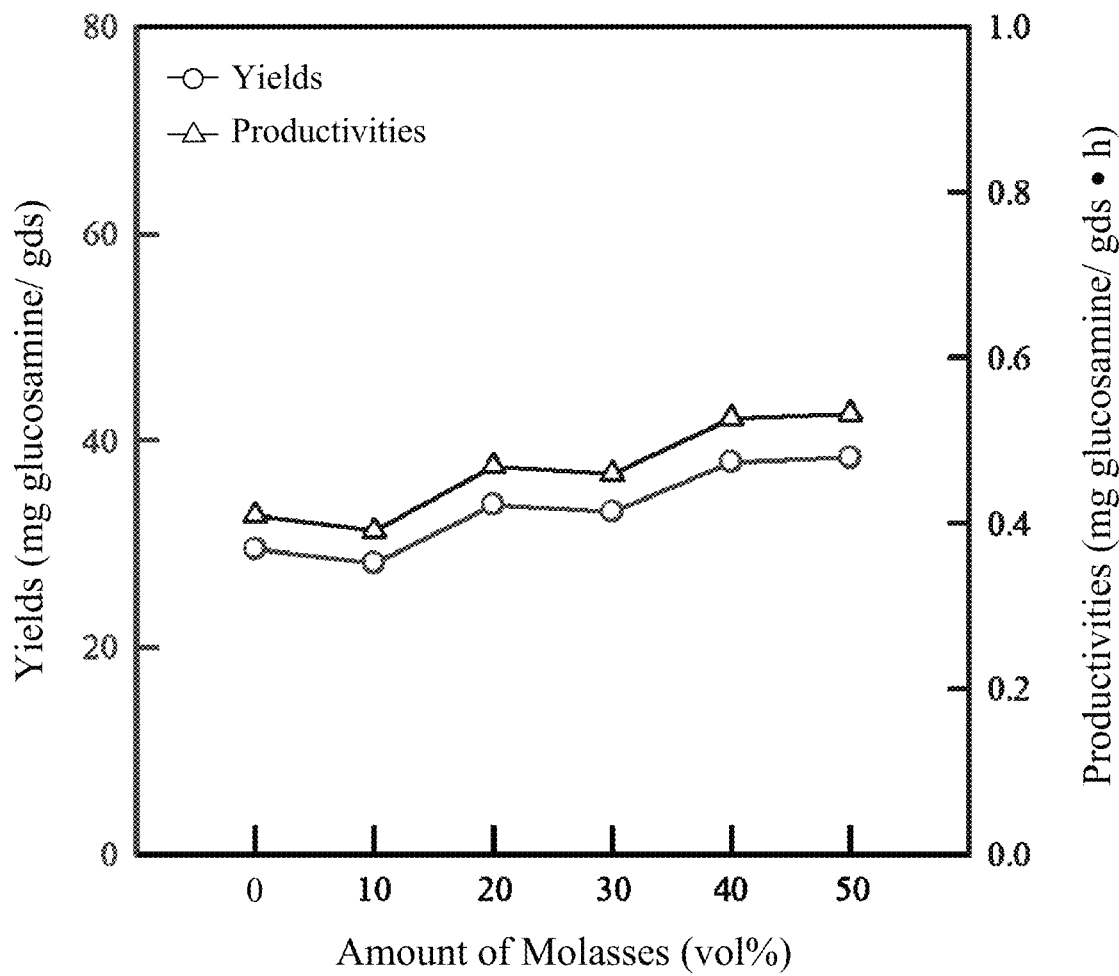
FIG. 8 shows the yields and productivities of glucosamine produced by *A. sydowii* BCRC 31742 cultivated in a solid medium containing wheat bran supplied with different amount of molasses for three days.

Treatment of the fungi and analysis method and conditions of HPLC are the same as those described in Example 1. Yield is calculated by dividing the amount of glucosamine obtained by the weight of dry substrate. Productivity is calculated by dividing the amount of the obtained glucosamine by the weight of dry substrate and incubation time. The results of yields and productivities of glucosamine produced by *A. sydowii* are shown in FIG. 8.

In this Example, addition of molasses is proved to increase productivity of glucosamine. In view of glucosamine productivity, additional amount of molasses is preferably 10-50 vol %, more preferably 50 vol %.

Example 8

Effects of Sequential Addition of Supplemental Solution on Fungal Growth

I. Fungal Fermentation Test

*A. sydowii* BCRC 31742 (Hsinchu, Taiwan) was also used in the tests of this Example. First, the fungi were recovered by being subcultured twice with the method described in Example 1.

After that, 6 mL of the recovered fungi were seeded on different glass petri dishes with a diameter of 9 cm by the following methods respectively:

(1) Mixing the 6 mL of the recovered fungi and 6 mL supplemental solution (containing 0.2 wt % $KH_2PO_4$, 0.1 wt % NaCl, and 0.1 wt % $MgSO_4.7H_2O$), and then the mixture was seeded on wheat bran solid medium (5 g sterilized wheat bran and 9 mL of the supplemental solution), wherein the final volume of the supplemental solution was 15 mL (equivalent to 3 mL/g substrate);

(2) Mixing the 6 mL of the recovered fungi and 3 mL supplemental solution (containing 0.2 wt % $KH_2PO_4$, 0.1 wt % NaCl, and 0.1 wt % $MgSO_4.7H_2O$), and then the mixture was seeded on wheat bran solid medium (5 g sterilized wheat bran and 12 mL of the supplemental solution), wherein the final volume of the supplemental solution was 15 mL (equivalent to 3 mL/g substrate); and (3) Seeding the 6 mL of the recovered fungi on wheat bran solid medium (5 g sterilized wheat bran and 15 mL supplemental solution containing 0.2 wt % $KH_2PO_4$, 0.1 wt % NaCl, and 0.1 wt % $MgSO_4.7H_2O$), wherein the final volume of the supplemental solution was 15 mL (equivalent to 3 mL/g substrate).

The fungi were incubated at 30° C. for 3 days, and then were subject to determination of glucosamine.

II. Determination of Glucosamine

Treatment of the fungi and analysis method and conditions of HPLC are the same as those described in Example 1. Yield is calculated by dividing the amount of glucosamine obtained by the weight of dry substrate. Productivity is calculated by dividing the amount of the obtained glucosamine by the weight of dry substrate and incubation time. The results of yields and productivities of glucosamine produced by A. sydowii are shown in Table 4. The results indicate that firstly adding 9 mL of supplemental solution (pre-inoculation) and then secondly adding 6 mL of supplemental solution (during inoculation) make the fungi have highest yields and productivities.

TABLE 4

Comparison of yields and productivities of glucosamine produced by A. sydowii with different sequential addition of supplemental solution

| Volume of supplemental solution added to solid medium (first addition) (mL) | Volume of supplemental solution mixed with inoculum (second addition to the solid medium) (mL) | Yield (mg/gds) | Productivity (mg/gds · h) |
|---|---|---|---|
| 9 | 6 | 29.5 | 0.41 |
| 9 | 6 | 29.2 | 0.40 |
| 12 | 3 | 26.4 | 0.36 |
| 12 | 3 | 27.2 | 0.37 |
| 15 | 0 | 22.5 | 0.31 |
| 15 | 0 | 25.3 | 0.35 |

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method for producing glucosamine, comprising:
providing a microorganism being able to produce glucosamine, wherein the microorganism is *Aspergillus sydowii*; and
fermenting the microorganism in a solid medium which comprises substrate and 0.15-4.8 mL/g substrate of supplemental solution;
wherein the substrate is wheat bran without alkaline pretreatment and the supplemental solution including
ental solution including
0.1-2 g/L $KH_2PO_4$;
0.1-2 g/L NaCl; and
0.1-2 g/L $MgSO_4.7H_2O$.

2. The method of claim 1, wherein the substrate is treated by high temperature, high pressure, or the combination thereof.

3. The method of claim 1, wherein the substrate is in a container and has a thickness of 0.5-2.5 mm.

4. The method of claim 1, wherein the microorganism has an inoculum amount of 9 to 36 mg/g substrate.

5. The method of claim 1, wherein the solid medium further comprises 5-50 percentage by volume of molasses, and the molasses is pretreated with the following steps: mixing a molasses stock with water at a ratio of 0.5:1 to 5:1 by volume, allowing the mixed molasses stock and water to settle and form an upper layer and a lower layer, and collecting the upper layer as treated molasses.

6. The method of claim 5, wherein the supplemental solution is divided into a first portion and a second portion, the first portion has 50-60 percentage by volume (vol %) of the supplemental solution, and the second portion has 40-50 vol % of the supplemental solution, and the first portion is added to the substrate before the second portion is added to the substrate.

7. The method of claim 1, wherein the microorganism is fermented for 48-120 hours.

8. The method of claim 1, wherein glucosamine is harvested when the microorganism begins to produce spore capsule.

* * * * *